United States Patent [19]

Mack et al.

[11] Patent Number: Plant 6,402

[45] Date of Patent: Nov. 15, 1988

[54] CHRYSANTHEMUM PLANT NAMED ENCORE

[75] Inventors: Grace H. Mack, 108 Wahackme Rd., New Canaan, Conn. 06840; Cornelis P. VandenBerg, Salinas, Calif.

[73] Assignee: Grace H. Mack, New Canaan, Conn.

[21] Appl. No.: 938,889

[22] Filed: Dec. 8, 1986

[51] Int. Cl.[4] ..... A01H 5/00

[52] U.S. Cl. ..... Plt./77

[58] Field of Search ..... Plt./77

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Encore particularly characterized by its flat capitulum form; decorative capitulum type; white ray floret color; diameter across face of capitulum of up to 6 cm at maturity; short plant height with spreading and prolific branching pattern; average natural season flower date of August 30 in Salinas, Calif. and September 24 in Hightstown, N.J. uniform seven week photoperiodic flowering response to short days in photoperiodic controlled flowering programs; and by its durable, uniform performance in outside fall flowerings and in spring small pot flowering programs.

3 Drawing Sheets

The present invention comprises a new and distinct cultivar of Chrysanthemum, botanically known as *Chrysanthemum morifolium*, Ramat., and referred to by the cultivar name Encore.

Encore, identified as 83M05009, was originated from a cross made by Grace H. Mack in a controlled breeding program in New Canaan, Conn., in 1982.

The female parent of Encore was the cultivar identified as Pearls, disclosed in U.S. Plant Pat. No. 3,970. The male parent of Encore was an unnamed seedling.

Encore was discovered and selected as one flowering plant within the progeny of the stated cross by Cornelis P. VandenBerg in September 1983, in a controlled environment in Salinas, Calif.

The first act of asexual reproduction of Encore was accomplished when vegetative cuttings were taken from the initial selection in December 1983 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Encore are firmly fixed and are retained through successive generations of asexual reproduction.

Encore has not been observed under all possible environmental conditions. The phenotype may vary significantly with variations in environment such as temperature, light intensity, and daylength.

The following observations, measurements and comparisons describe plants grown in a controlled open area in Salinas, Calif. and in Hightstown, N.J. Rooted cuttings were established in soil and maintained outdoors under the natural temperature and daylength prevailing during July through September. Single pinching was practiced with all branches and buds retained.

The following traits have been repeatedly observed and are determined to be basic characteristics of Encore, which, in combination, distinguish this Chrysanthemum as a new and distinct cultivar:

1. Flat capitulum form.
2. Decorative capitulum type.
3. White ray floret color.

4. Diameter across face of capitulum up to 6 cm at maturity.
5. Short plant height.
6. Spreading and prolific branching pattern.
7. Average natural season flower date of August 30 in Salinas, Calif., and September 24 in Hightstown, N.J.
8. Uniform seven week photoperiodic flowering response to short days in photoperiodic controlled flowering programs.
9. Durable, uniform performance in outside fall flowerings and in spring small pot flowering programs.

The accompanying photographic drawings show typical inflorescence and leaf characteristics of Encore, with the colors being as nearly true as possible with illustrations of this type.

Sheet 1 is a color photograph of Encore grown as a pinched spray pot mum.

Sheet 2 is a black and white photograph of three views of the inflorescence of Encore.

Sheet 3 is a black and white photograph showing the upper and under sides of the leaves of Encore at three stages of development (Mature, intermediate and immature).

Of the commercial cultivars known to the inventors, the most similar in comparison to Encore is White Grandchild, an unpatented garden mum cultivar. Reference is made to attached Chart A, which compares certain characteristics of Encore to the same characteristics of White Grandchild.

Traits similar to both Encore and White Grandchild are capitulum form and type, ray floret color, diameter across face of capitulum, and flowering response. Encore has a pure white flowering, and shows no pinking as seen in White Grandchild. Also, Encore is shorter, with a more spreading and prolific branching pattern than White Grandchild.

In the following description, color references are made to the Royal Horticultural Society Colour Chart. The clear white ray floret color of Encore is not represented in the R.H.S. Colour Chart. The color values were determined on plant material grown outside in Salinas, Calif. on Aug. 25, 1986.

Classification:

*Botanical.*—*Chrysanthemum morifolium,* Ramat., cv. Encore.

*Commercial.*—Decorative spray pot mum and garden mum.

INFLORESCENCE

A. Capitulum:

*Form.*—Flat.

*Type.*—Decorative.

*Diameter across face.*—Up to 6 cm at maturity.

B. Corolla of ray florets:

*Color (general tonality from a distance of three meters).*—White.

*Color (upper surface).*—White.

*Color (under surface).*—White.

*Shape.*—Oblong.

C. Corolla of disc florets:

*Color (mature).*—3A.

*Color (immature).*—154B.

D. Reproductive organs:

*Androecium.*—Present on disc florets only; scant pollen.

*Gynoecium.*—Present on both ray and disc florets.

PLANT

A. General appearance:

*Height.*—Short.

*Branching pattern.*—Spreading and prolific.

B. Foliage:

*Color (upper surface).*—137A to 137B.

*Color (under surface).*—137A to 137B.

*Shape.*—Lobed and serrated.

CHART A

COMPARISON OF ENCORE AND WHITE GRANDCHILD

| CULTIVAR | RAY FLORET COLOR | CAPITULUM FORM AND TYPE | BRANCHING PATTERN |
|---|---|---|---|
| ENCORE | WHITE | FLAT DECORATIVE | SPREADING AND PROLIFIC |
| WHITE GRAND-CHILD | WHITE | FLAT DECORATIVE | SEMI SPREADING |

CHART A-continued

| CULTIVAR | DIAMETER ACROSS FACE OF CAPI-TULUM | PLANT HEIGHT | AVERAGE NATURAL SEASON FLOWER DATE SALINAS, CALIFORNIA |
|---|---|---|---|
| ENCORE | 6 cm. | SHORT | AUGUST 30 |
| WHITE GRAND-CHILD | 6 cm. | MEDIUM | SEPTEMBER 2 |

| CULTIVAR | AVERAGE NATURAL SEASON FLOWER DATE HIGHTSTOWN, NEW JERSEY | CONTROLLED RESPONSE |
|---|---|---|
| ENCORE | SEPTEMBER 24 | SEVEN WEEKS |
| WHITE GRANDCHILD | SEPTEMBER 24 | SEVEN WEEKS |

COMPARISON MADE OF PLANTS GROWN UNDER NATURAL SEASON OUTDOOR CONDITIONS IN SALINAS, CALIFORNIA AND HIGHTSTOWN, NEW JERSEY

We claim:

1. A new and distinct Chrysanthemum plant named Encore, as described and illustrated, and particularly characterized as to uniqueness by the combined characteristics of flat capitulum form; decorative capitulum type; white ray floret color; diameter across face of capitulum of up to 6 cm at maturity; short plant height with spreading and prolific branching pattern; average natural season flower date of August 30 in Salinas, Calif. and September 24 in Hightstown, N.J.; uniform seven week photoperiodic flowering response to short days in photoperiodic controlled flowering programs; and durable, uniform performance in outside fall flowerings and in spring small pot flowering programs.

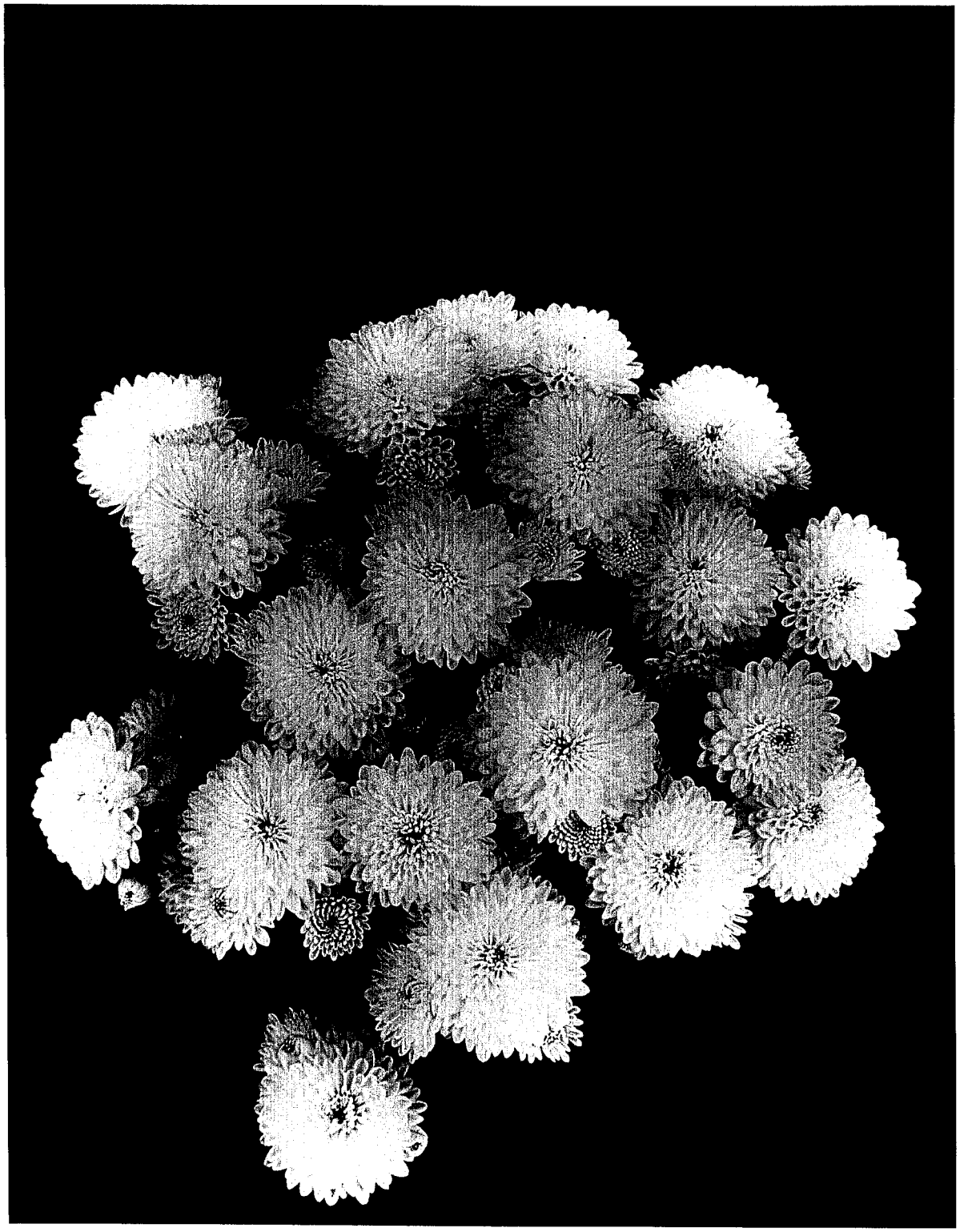

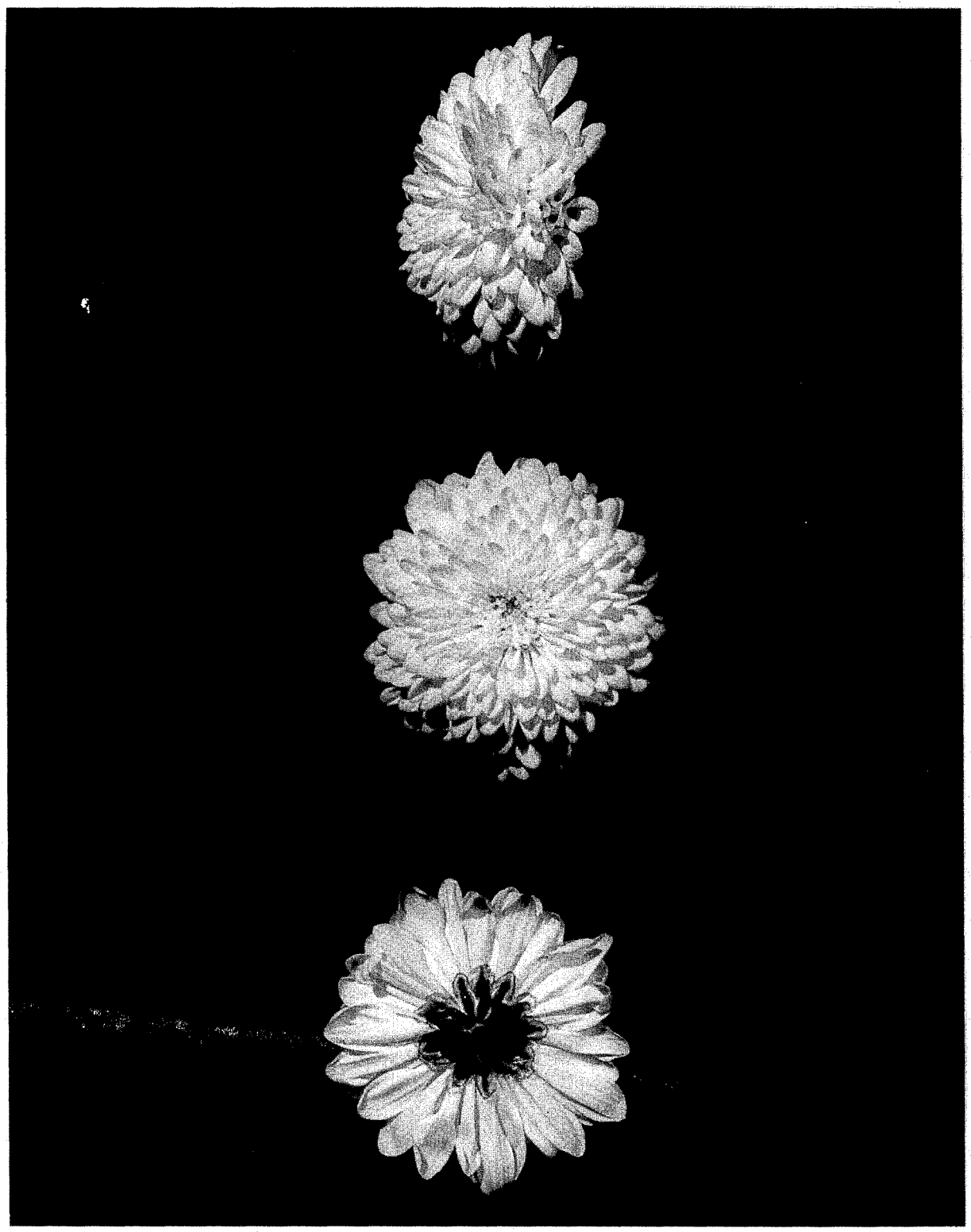

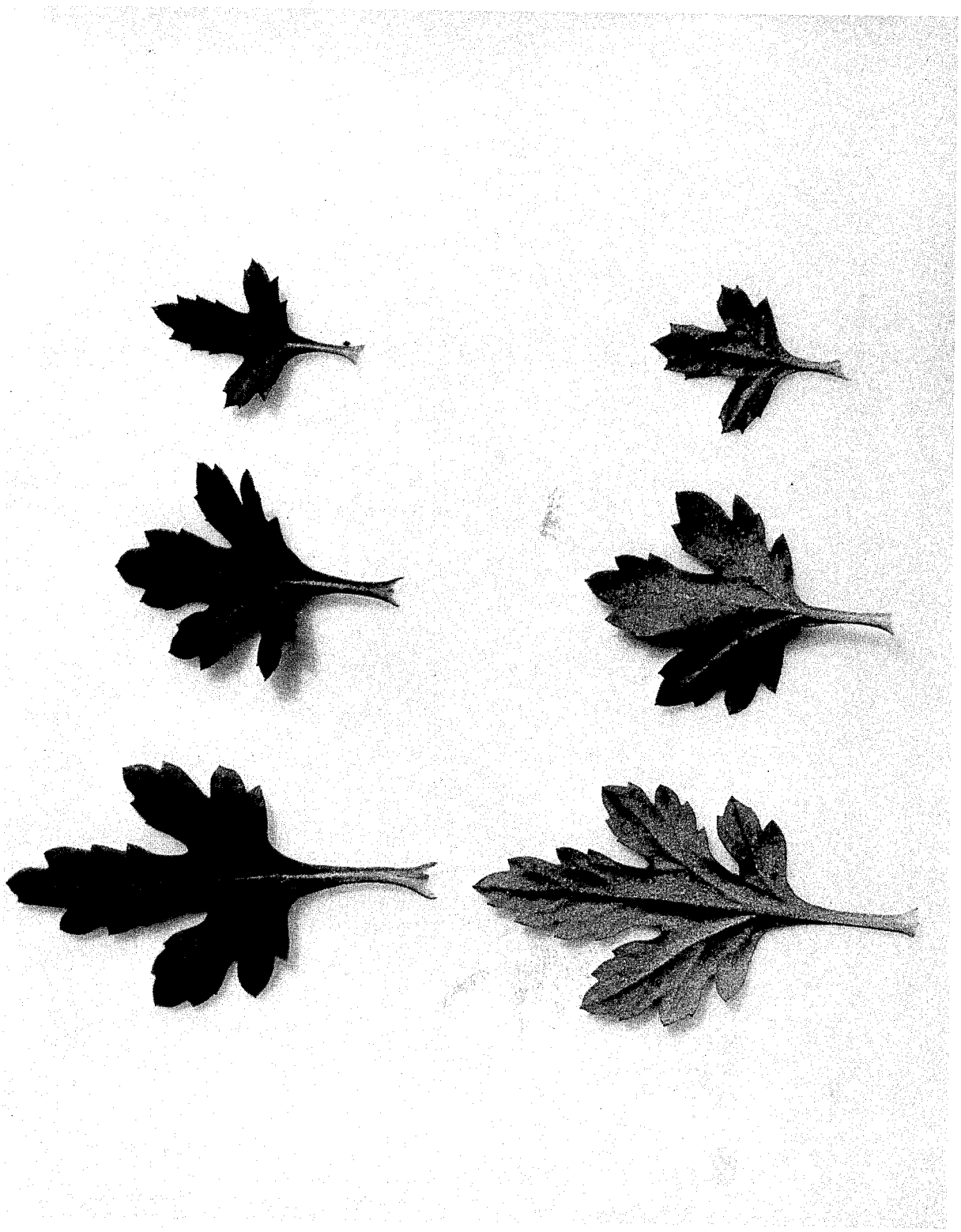

* * * * *